United States Patent [19]

Hazen

[11] Patent Number: 4,769,182

[45] Date of Patent: Sep. 6, 1988

[54] PROCESS FOR PRODUCTION OF 3-(HYDROXYPHENYLPHOSPHINYL)-PROPANOIC ACID

[75] Inventor: James R. Hazen, Coventry, R.I.

[73] Assignee: Hoechst Celanese Corporation, N.J.

[21] Appl. No.: 741,060

[22] Filed: Jun. 5, 1985

[51] Int. Cl.$^4$ ................................................ C07F 9/30
[52] U.S. Cl. ........................ 260/502.4 R; 260/544 R; 260/545 P
[58] Field of Search ................................ 260/502.4 D

[56] References Cited

U.S. PATENT DOCUMENTS 4,081,463  3/1978  Birum et al. ................ 260/502.4 D

OTHER PUBLICATIONS

Pudovik et al., "Zhur. Obsch. Khim., 37", No. 2, (1967), pp. 423–427, Translation.

Primary Examiner—J. E. Evans
Attorney, Agent, or Firm—Hugh C. Crall; John P. Blasko

[57] ABSTRACT

3-(Hydroxyphenylphosphinyl)-propanoic acid is produced by reacting phenylphosphonous dichloride with a 0 to 20 percent molar excess of acrylic acid at a temperature of 60° to 150° C., heating the reaction mixture at a temperature of 115° to 150° for at least 45 minutes, and then hydrolyzing the mixture to obtain the desired product.

16 Claims, No Drawings

PROCESS FOR PRODUCTION OF 3-(HYDROXYPHENYLPHOSPHINYL)-PROPANOIC ACID

BACKGROUND OF THE INVENTION 3-(Hydroxyphenylphosphinyl)-propanoic acid, 3-HPP (I), which imparts flame retardant properties to polymers such as polyesters into which it is incorporated, has previously been prepared by reacting acrylic acid (II) and phenylphosphonous dichloride, PPD (III), in a condensation reaction, followed by the hydrolysis of the condensation mixture to give the product, according to the following scheme:

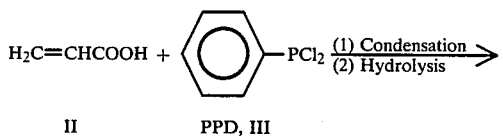

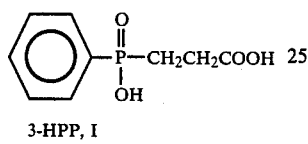

3-HPP, I

For example, Pudovik et al. [Russian Journal of Organic Chemistry, Vol. 37, pp. 423–427 (1967)] reported conducting the condensation reaction at temperatures up to 95°–100° C. and isolating the 3-(chlorophenylphosphinyl)-propionyl chloride (IV) as the condensation product in moderate (77%) yield by distillation. Subsequent hydrolysis of

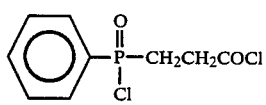

gave the desired product (I) in an overall yield of 71%.

An improved process was reported by Birum et al. in U.S. Pat. No. 4,081,463, the improvement being manifested as a greatly increased overall yield of at least 89.6% of (I) after hydrolysis. The basis of the Birum patent is the claim that the enhanced yield is achievable only when a very specific ratio of reactants is used in the condensation step, namely, a 25–45% molar excess, preferably 30–40% excess, of the acrylic acid (II) with respect to phenylphosphonous dichloride (III). It is further taught that if this critical and specific ratio of reactants is not utilized, as for example where equimolar quantities of reactants are employed, the yield of the desired 3-HPP (I) is unsatisfactorily low and, furthermore, that the product is impure and difficult to purify.

The stated explanation for these undesirable phenomena is that where only equimolar quantities of reactants are used the resulting condensation mixture still contains a substantial amount (ca. 25%) of unconverted PPD (III). By contrast, the condensation mixture resulting from the use of a large initial excess of acrylic acid (II) contains no residual PPD (III), but rather a mixture of three intermediates all of which are hydrolyzable to the desired product (I). These intermediates include not only the expected condensation product (IV), but also the corresponding cyclic anhydride (V) and the mixed anhydride (VI):

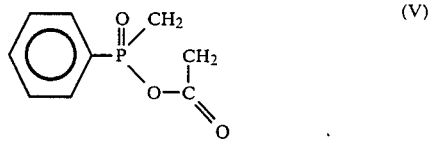

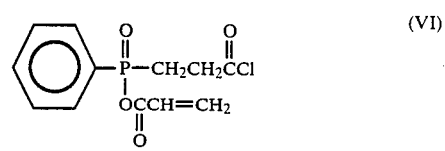

Hence it is taught that it is critical to use the initial 25–45% molar excess of acrylic acid (II) to completely convert all of the PPD (III) and thereby generate the necessary mixture of intermediates (IV), (V) and (VI) to give the maximum yield of 3-HPP (I).

SUMMARY OF THE INVENTION

An improved process has now been found in which the condensation reaction can be conducted without using a substantial excess of acrylic acid (II) relative to phenylphosphonous dichloride (III), while maintaining high yields of very pure product, 3-(hydroxyphenylphosphinyl)-propanoic acid (I).

Thus it has been found that when PPD (III) is condensed with only an equimolar quantity or a slight excess of acrylic acid (II), in particular a 0–20% molar excess, preferably a 0–10% excess, more preferably a 5–8% excess, a mixture is obtained which upon heating to 115°–150° C., preferably 120°–130° C., undergoes a secondary reaction or reactions which consume virtually all the phenylphosphonous dichloride (III). Upon hydrolysis of this mixture, preferably with the wash water from a previous reaction, a substantially quantitative yield of very pure, snow-white 3-(hydroxyphenylphosphinyl)-propanoic acid (I) is obtained.

In contrast with this invention, if the condensation mixture is not heat treated above 115° C., the unconverted PPD (III) will remain and, upon hydrolysis, will be lost as phenylphosphinic acid, resulting in a low yield of the desired 3-HPP (I) in an impure form.

It is an object of this invention, and significant advantage over the prior art, to reduce the consumption of acrylic acid (II) relative to prior art methods by about 30–40% while still achieving equivalent product yield and purity.

It is a further object of this invention to virtually eliminate organic matter, the chief source of which is acrylic acid, from the waste water discharge from the process, thereby minimizing waste treatment costs and capacity utilization.

DETAILED DESCRIPTION OF THE INVENTION

While the methodology of this new process is seemingly very simple, the key difference being a heat treatment which allows the reaction to be run at near equimolar quantities of reactants, this technique is conceptually unobvious from the prior art because of a heretofore incomplete understanding of the complexity of all the chemical pathways occurring in the condensation. In particular, until the present invention, there has been an incomplete understanding of the critical role of acrylic acid in the various reaction pathways leading to 3-HPP besides the direct reaction with PPD.

The chemical complexity of the condensation step is taught by Birum et al., albeit incompletely, in their finding of a number of phosphorous-containing intermediates besides the expected (IV) and by finding much unconverted starting PPD even after reaction with an equimolar amount of acrylic acid. It was thus implied, without explanation by Birum et al., that a substantial percentage of the acrylic acid is being consumed in secondary, undefined reaction pathways which thus leave a deficiency of acrylic acid relative to PPD. Birum et al. solve the problem of the acrylic acid deficiency simply by utilizing a much greater initial molar excess of acrylic acid in the reaction. In focusing on the phosphorous-containing intermediates, the full implications of the deficiency are ignored and it is assumed that the acrylic acid is irretrievably lost. The one product which does partially explain the secondary consumption of acrylic acid, i.e., the mixed anhydride (IV), is formed in insufficient amount to account for the overall deficiency of acrylic acid in the condensation mixture.

In the present invention, however, it has been found that (1) the acrylic acid is not actually lost or unavailable, but rather only masked by conversion to one or more other derivatives during the condensation, and, most importantly, that (2) these masked acrylic acid derivatives can be made to react with any unconverted PPD under the forcing conditions of a heat-up cycle or heat treatment.

The secondary reactions of acrylic acid during the condensation step are, in fact, intimately intertwined with the chemistry of the phosphorous-containing intermediates, and involve mainly acid-acid chloride exchange reactions and mixed anhydride formation. For example, it is known [Khairullin et al., Otd. Obschch. Tekh. Khim. 1967, 35; C.A., vol. 69, 59329 (1968)] that the formation of cyclic anhydride (V) proceeds via the reaction of acrylic acid with the primary condensation intermediate (IV) to generate acryloyl chloride and HCl. The formation of the mixed anhydride (VI) by the reaction of (IV) with acrylic acid also liberates HCl. Furthermore, it has now been found that the liberated HCl is not evolved from the condensation mixture nor dissolved in it, but rather rapidly reacts further with free acrylic acid and/or its acid chloride to yield 3-chloropropionic acid and its acid chloride. There may be similar and related interconversions among the other components of the condensation mixture to generate these same acrylic acid derivatives.

However, the present invention is not just the elucidation of the pathways by which the free acrylic acid is converted to other derivatives, but rather the finding that these derivatives, in particular 3-chloropropionic acid, serve as acrylic acid synthons or equivalents under the appropriate reaction conditions in condensations with PPD. For example, this may be independently demonstrated by a suitable control condensation in which as much as 20-30% of the one equivalent of acrylic acid may be substituted with authentic 3-chloropropionic acid without affecting the overall yield of the final desired product, 3-HPP (I), as long as the condensation mixture is subjected to the heating cycle. Thus it can be shown that not only does 3-chloropropionic acid, for example, form in the condensation reaction mixture, but it also can react with PPD to give 3-HPP after hydrolysis. A key point is that these derivatives, such as 3-chloropropionic acid and presumably acryloyl chloride and 3-chloropropionyl chloride, are masked equivalents of acrylic acid and are still reactive towards PPD, however, at much lower rate than acrylic acid itself.

The heating cycle thus permits these less reactive derivatives to react completely, thereby completely utilizing virtually all of the initial input of acrylic acid without resorting to the use of a large molar excess of acrylic acid. These results are entirely consistent with a low (ca. 71%) yield of 3-HPP using about a 1:1 mole ratio of reactants at temperatures of about 100° C. and a substantially higher yield (>90%) at temperatures of about 115° and higher.

The above detailed explanation of the fundamental theoretical and experimental foundations of the invention demonstrate that because the chemistry of the condensation was previously incompletely understood, the invention, while simple, is novel and by no means anticipated by or obvious from the prior art.

DESCRIPTION OF THE PREFERRED EMBODIMENTS

There are a range of options available for the precise manner in which the condensation reaction, heat treatment and hydrolysis may be conducted accordng to the present invention.

The condensation is conducted by reacting PPD with a 0-20% molar excess of acrylic acid, preferably a 0-10% excess, more preferably a 5-8% excess. The temperature for the condensation is in the range of approximately 60°-150° C. as long as the last part of the reaction is conducted at a temperature of at least about 115° C. The entire condensation reaction may be carried out at about 115° C. or greater. However, the preferred method is to add the acrylic acid in a controlled manner to the hot PPD at about 60°-110° C., most preferably at 75°-110°, followed by raising the temperature to approximately 115°-150° C., most preferably 120° C.-130° C. The time for the heating period is about 45 minutes or longer, most preferably 45-90 minutes.

The hydrolysis of the condensation mixture is typical of the hydrolysis conditions for acid chlorides and similar water-reactive species and is documented in the prior art. A preferred drowning technique, however, is to use the wash water, separate from the mother liquors, of a previous reaction as the drowning medium, instead of water alone. By this means the recovery of 3-HPP is increased 5-6%, which could otherwise only be obtained by the evaporation of the wash to near dryness. Whereas it is a customary technique to recycle or re-use reaction mother liquors in this manner to enhance product recovery, in the present invention the use of the mother liquor is unsatisfactory. Thus, when the mother liquor is recycled, the drowning is troublesome due to excessive gaseous HCl liberation, the product yield is not enhanced, and the product purity is diminished. In the present invention, it is, unexpectedly, the wash water rather than the mother liquor which contains most of the product and from which it is recoverable by recycling.

The following example is illustrative of the invention, but is not limitative of the scope of the invention.

EXAMPLE 1

Phenylphosphonous dichloride, 329 g (1.84 moles), is heated to 80° C. with stirring and then treated in a controlled, dropwise manner with acrylic acid, 142 g (1.97 moles). The heat of reaction is used to maintain the temperature during the addition at 80° C. with external cooling as necessary. When the addition is complete the mixture is maintained briefly at about 80° C. and then heated further to 125°-130° C. The mixture is maintained at 125°-130° C. for one hour and then cooled to ambient temperature. The condensation mixture is then drowned into 850 ml of the wash water from a previous reaction, allowing the temperature to rise to 90° C. The clear, colorless, homogeneous solution is cooled to 70° C., at which temperature the product starts to precipitate. The white slurry is cooled to below 5° C., held for one hour, and filtered. The mother liquor is discarded. The product is washed with 750 ml water in three portions and the resulting wash water saved for recycling into a subsequent reaction. The wet product is dried to give 372 g (94.5% yield) of 3-(hydroxyphenylphosphinyl)-propanoic acid (I) as a snow-white microcrystalline powder.

I claim:

1. A process for the production of 3-(hydroxyphenylphosphinyl)propanoic acid comprising:

mixing phenylphosphonous dichloride with about 5 to 10% molar excess of acrylic acid at a temperature of 60° to 150° C.;

heating said mixture at a temperature of 115° to 150° C. until virtually all of said phenylphosphonous dichloride is consumed in reaction; and hydrolyzing said mixture in water.

2. A process as in claim 1 wherein the phenylphosphonous dichloride is mixed with about 5 to 8 molar excess of acrylic acid.

3. A process as in claim 1 wherein the mixture is hydrolyzed in the until virtually all of said phenylphosphonous dichloride is consumed in reaction from a previous reaction.

4. A process as in claim 2 wherein the mixture is hydrolyzed in the until virtually all of said phenylphosphonous dichloride is consumed in reaction from a previous reaction.

5. A process as in claim 1 wherein the phenylphosphonous dichloride is mixed with the acrylic acid at a temperature of 60° to 110° C.

6. A process as in claim 3 wherein the phenylphosphonous dichloride is mixed with the acrylic acid at a temperature of 60° to 100° C.

7. A process as in claim 3 wherein the phenylphosphonous dichloride is mixed with the acrylic acid at a temperature of 60° to 110°.

8. A process as in claim 4 wherein the phenylphosphonous dichloride is mixed with the acrylic acid at a temperature of 60° to 110° C.

9. A process as in claim 1 wherein said mixture is heated for at least 45 minutes.

10. A process as in claim 2 wherein said mixture is heated for at least 45 minutes.

11. A process as in claim 3 wherein said mixture is heated for at least 45 minutes.

12. A process as in claim 4 wherein said mixture is heated for at least 45 minutes.

13. A process as in claim 5 wherein said mixture is heated for at leasst 45 minutes.

14. A process as in claim 6 wherein said mixture is heated for at least 45 minutes.

15. A process as in claim 7 wherein said mixture is heated for least 45 minutes.

16. A process as in claim 8 wherein said mixture is heated for at least 45 minutes.

* * * * *

UNITED STATES PATENT AND TRADEMARK OFFICE
CERTIFICATE OF CORRECTION

PATENT NO. : 4,769,182
DATED : September 6, 1988
INVENTOR(S) : James R. Hazen

It is certified that error appears in the above-identified patent and that said Letters Patent is hereby corrected as shown below:

Column 2: Insert a bond between the methylene groups at Roman numeral (V)

Column 3: Line 21 "(IV)" should read (VI)

Column 4: Line 26: "accordng" should read according

Column 5: Line 35: delete "the until virtually all of said phenylphos-" and

Column 6: Line 1 : delete phonous dichloride is consumer in reaction"

Insert: wash water which has been used to wash the product

Column 6: Line 4: delete "the until virtually all of said phenylphos-"

Column 6: Line 5: delete "phonous dichloride is consumed in reaction"

Insert: wash water which has been used to wash the product

UNITED STATES PATENT AND TRADEMARK OFFICE
CERTIFICATE OF CORRECTION

PATENT NO. : 4,769,182

DATED : September 6, 1988

INVENTOR(S) : James R. Hazen

It is certified that error appears in the above-identified patent and that said Letters Patent is hereby corrected as shown below:

Column 6: Line 10: "3" should read 2

Column 6: Line 12: "100°" should read 110°

Signed and Sealed this

Twenty-first Day of February, 1989

Attest:

DONALD J. QUIGG

*Attesting Officer*  *Commissioner of Patents and Trademarks*